(12) United States Patent
Merz et al.

(10) Patent No.: US 10,368,730 B2
(45) Date of Patent: Aug. 6, 2019

(54) LARYNGOSCOPE

(71) Applicant: Karl Storz SE & Co. KG, Tuttlingen (DE)

(72) Inventors: Ulrich Merz, Villingen-Schwenningen (DE); Juerg Attinger, Stein am Rhein (CH); Eugenia Fuhr, Tuttlingen (DE); Thomas Breinlinger, Emmingen-Liptingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 15/417,985

(22) Filed: Jan. 27, 2017

(65) Prior Publication Data

US 2017/0258311 A1 Sep. 14, 2017

(30) Foreign Application Priority Data

Feb. 5, 2016 (DE) .................. 10 2016 001 309

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00066* (2013.01); *A61B 1/00101* (2013.01); *A61B 1/00154* (2013.01); *A61B 1/012* (2013.01); *A61B 1/0125* (2013.01); *A61B 1/04* (2013.01); *A61B 1/053* (2013.01)

(58) Field of Classification Search
CPC ...................................................... A61B 1/267
See application file for complete search history.

(56) References Cited

U.S. PATENT DOCUMENTS 3,926,196 A * 12/1975 Bornhorst .............. A61B 1/267
128/207.14
5,499,983 A * 3/1996 Hughes ................. A61B 17/701
403/298

(Continued)

FOREIGN PATENT DOCUMENTS

| DE | 19955180 B4 | 12/2000 |
| WO | 9927840 A1 | 6/1999 |
| WO | 2016074894 A2 | 5/2016 |

OTHER PUBLICATIONS

German Search Report Application No. 10 2016 001 309.5 Completed: Sep. 6, 2016; dated Sep. 9, 2016 8 Pages.

(Continued)

*Primary Examiner* — Jan Christopher L Merene
(74) *Attorney, Agent, or Firm* — Whitmyer IP Group LLC

(57) ABSTRACT

A laryngoscope with a handle, at the distal end of which a blade is arranged at an angle to the longitudinal axis of the handle, wherein a channel for receiving an image carrier of a video endoscope is formed in the handle and in the blade such that the channel, in a transition area from the handle to the blade, merges in a radius from the handle into the blade. In order to provide a laryngoscope which, while being easy to handle, ensures insertion of the image carrier into the channel in a way that protects material, in the transition area from the handle into the blade, at least one run-on bevel is formed in the interior of the channel.

11 Claims, 3 Drawing Sheets

(51) Int. Cl.
*A61B 1/012* (2006.01)
*A61B 1/04* (2006.01)
*A61B 1/05* (2006.01)

(56) References Cited

U.S. PATENT DOCUMENTS

| | | | | |
|---|---|---|---|---|
| 6,673,073 B1* | 1/2004 | Schafer | ............. | A61B 17/7049 606/250 |
| 2003/0181789 A1* | 9/2003 | Mazzei | ................. | A61B 1/267 600/188 |
| 2004/0122292 A1* | 6/2004 | Dey | .................... | A61B 1/0676 600/190 |
| 2005/0143770 A1* | 6/2005 | Carter | ................... | A61B 1/018 606/170 |
| 2007/0106121 A1* | 5/2007 | Yokota | ............... | A61B 1/00052 600/188 |
| 2009/0264933 A1* | 10/2009 | Carls | ................. | A61B 17/7001 606/264 |
| 2010/0168521 A1* | 7/2010 | Acha Gandarias | .. | A61B 1/0008 600/188 |
| 2010/0261967 A1* | 10/2010 | Pacey | ................ | A61B 1/00103 600/186 |
| 2013/0060089 A1* | 3/2013 | McGrath | ................ | A61B 1/267 600/187 |
| 2013/0104884 A1* | 5/2013 | Vazales | .................. | A61B 1/267 128/202.16 |
| 2013/0123851 A1* | 5/2013 | Seme | ..................... | A61B 17/70 606/250 |
| 2014/0107422 A1* | 4/2014 | Huels | ................. | A61B 1/00105 600/188 |
| 2014/0160261 A1* | 6/2014 | Miller | ............... | A61B 1/00052 348/77 |
| 2016/0206188 A1* | 7/2016 | Hruska | ............. | A61B 1/00052 |
| 2016/0220106 A1* | 8/2016 | Pecherer | ............... | A61B 1/267 |
| 2017/0196445 A1* | 7/2017 | Gardner | ............ | A61M 16/0445 |
| 2017/0360371 A1* | 12/2017 | Hacker | ............ | A61M 16/0488 |

OTHER PUBLICATIONS

European Search Report Application No. 17000129.1 Completed Date: Jun. 28, 2017; dated Jul. 10, 2017 7 Pages.
EndoWorld AN 92.0 C-MAC S, C-MAC S, Karl Storz GmbH & Co. KG, pp. 1-24, Jan. 2016.

* cited by examiner

LARYNGOSCOPE

TECHNICAL FIELD

The invention relates to a laryngoscope with a handle, at the distal end of which a blade is arranged at an angle to the longitudinal axis of the handle, wherein a channel for receiving an image carrier of a video endoscope is formed in the handle and in the blade such that the channel, in a transition area from the handle to the blade, merges in a radius from the handle into the blade.

BACKGROUND

Laryngoscopes are used for direct viewing and examination of the larynx. A laryngoscope of the type in question is known from DE 199 55 180 B4, for example. In the known laryngoscope, designed as a video laryngoscope, the image carrier serves to capture an image in the area of the distal end of the blade and to transmit said image to an image reproduction unit spatially separate from the blade. In video laryngoscopes, the image carrier is generally composed of a cable with a video chip arranged at the distal end of the latter.

Since the blade at the distal end of the handle is arranged substantially at right angles to the longitudinal axis of the handle, the channel formed in the handle and in the blade, and serving to receive the image carrier of a video endoscope, also has a strong curvature in the transition area from the handle to the blade, said curvature being configured in practice as a radius.

An example of a video laryngoscope of the type in question is the C-MAC® S from Karl Storz GmbH & Co. KG.

When inserting the image carrier of a video endoscope into the channel, there is a danger of the image carrier buckling in the angled transition area from the handle into the blade, which can result in permanent damage to the image carrier and, consequently, deterioration of the image transmission.

SUMMARY

Proceeding from this, it is the object of the invention to configure a laryngoscope which, while being easy to handle, ensures that the image carrier is inserted into the image carrier channel in a way that protects material.

According to the invention, the solution to this problem is characterized in that, in the transition area from the handle into the blade, at least one run-on bevel is formed in the interior of the channel.

By means of a run-on bevel being formed according to the invention in the interior of the channel and serving as a guide for the image carrier, it is possible for the first time to guide the image carrier around tight radii without buckling.

According to a practical embodiment of the invention, it is proposed that the run-on bevel is composed of several ribs arranged at a distance from one another. This design reduces the weight, since less material needs to be used for the run-on bevel, and, by virtue of the ribs extending parallel to one another, it additionally provides very good guiding of the image carrier that is to be inserted into the channel. Advantageously, the ribs arranged at a distance from one another are oriented parallel to one another.

With a preferred embodiment for forming the ribbed run-on bevel, it is proposed that that the ribs, viewed in the direction of insertion of the image carrier, are arranged on the inner wall of the channel at a location proximal from the strongest curvature of the radius. This arrangement of the ribs before the strongest curvature, as viewed in the direction of insertion, ensures that the image carrier is guided at the correct angle, and without risk of buckling, into the transition area between handle and blade.

To facilitate the targeted insertion of the image carrier into the channel, it is further proposed, according to the invention, that the ribs are oriented at an angle with respect to the longitudinal axis of the handle. The angled orientation of the ribs is such that the ribs are arranged on the inner wall of the channel facing into the radius.

According to the invention, the correctly positioned insertion of the image carrier into the channel can be further facilitated if the ribs also narrow the inside diameter of the channel, since they have an increasing radial thickness along their axial length from proximal to distal.

It is further proposed according to the invention that the ribs are formed all the way round the entire circumference of the inner wall of the channel.

According to an alternative embodiment of the invention, it is proposed that the ribs are formed only in sections about the circumference of the inner wall of the channel. In the case of the only sectional arrangement of the ribs, they can be divided up into one or more sections about the circumference of the inner wall of the channel.

The angle at which the blade is angled with respect to the longitudinal axis of the handle is preferably 70° to 90°.

Finally, it is proposed according to the invention that the handle and the blade are connected to each other releasably. This embodiment allows differently shaped blades to be used while retaining the handle.

Although laryngoscopes are in practice made from a plastics material and produced in one piece or composed of two shells and often used as disposable articles, this two-part embodiment may be expedient for stocking the broadest possible range of laryngoscope shapes.

BRIEF DESCRIPTION OF THE DRAWINGS

Further features and advantages of the invention will become clear from the appended drawings in which an illustrative embodiment of a laryngoscope according to the invention is depicted only by way of example, without limiting the invention to this illustrative embodiment. In the drawings.

DETAILED DESCRIPTION

Figure 1:
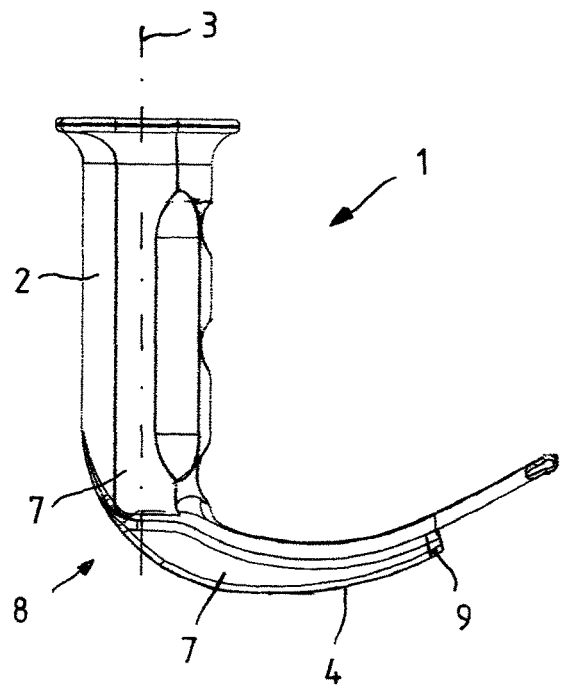
FIG. 1 shows a side view of a laryngoscope according to the invention with an associated video endoscope, before they are joined together.
Figure 1:
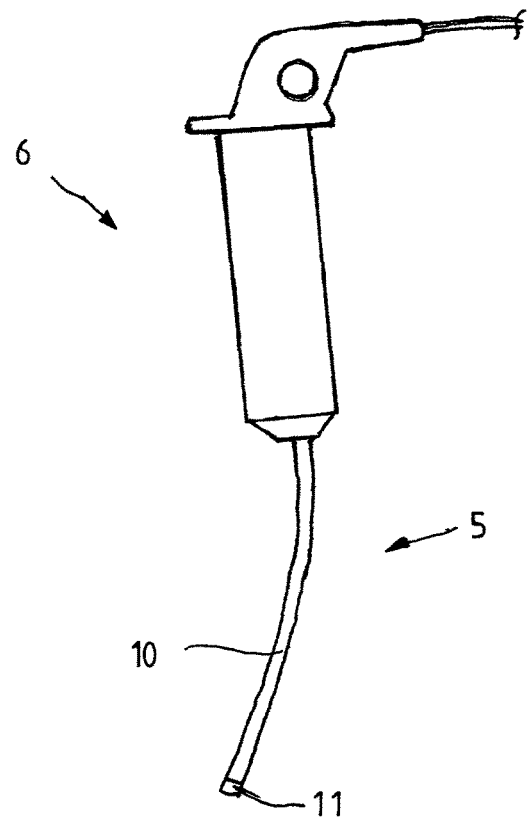
Figure 2:
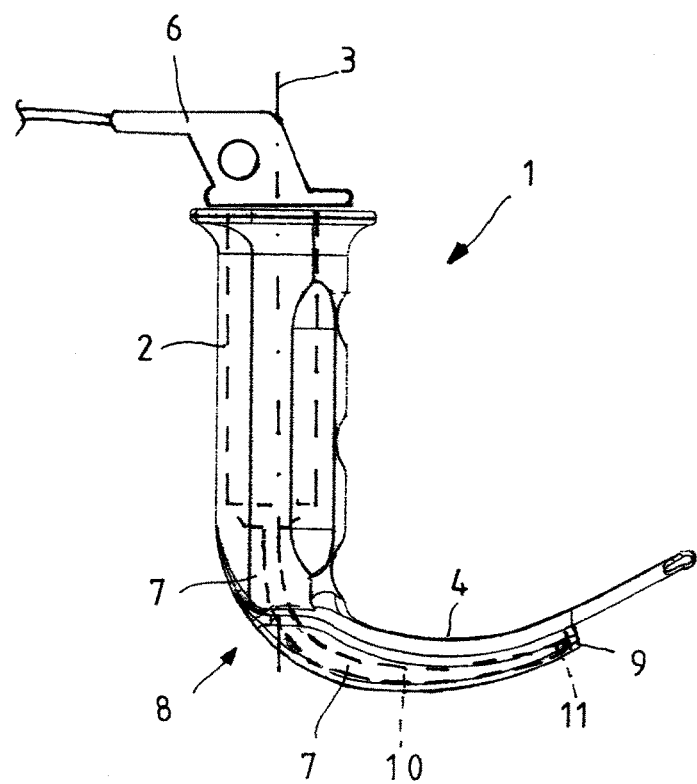
FIG. 2 shows a side view as per FIG. 1, but with the video endoscope inserted in the laryngoscope.
Figure 3A:
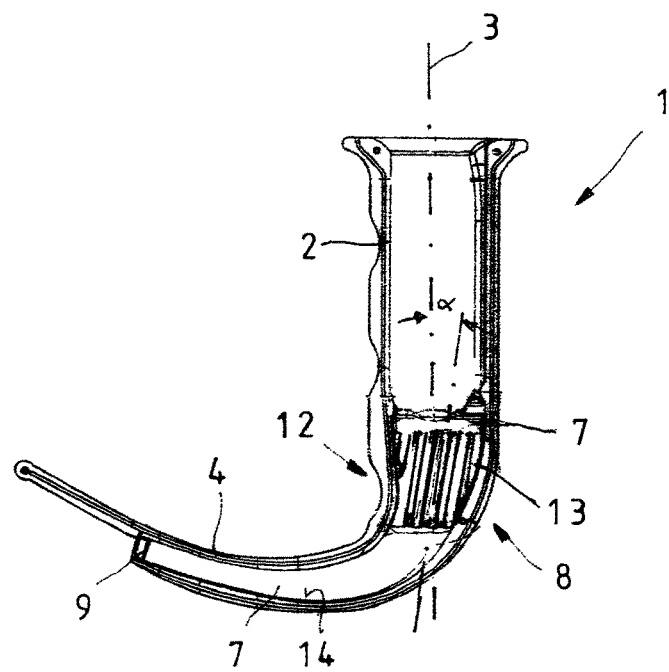
FIG. 3A shows a side view of the laryngoscope as per FIG. 1 in cross section and rotated through 90°, the laryngoscope having ribs arranged side by side around an entire circumference of the inner channel wall of the laryngoscope.
Figure 3B:
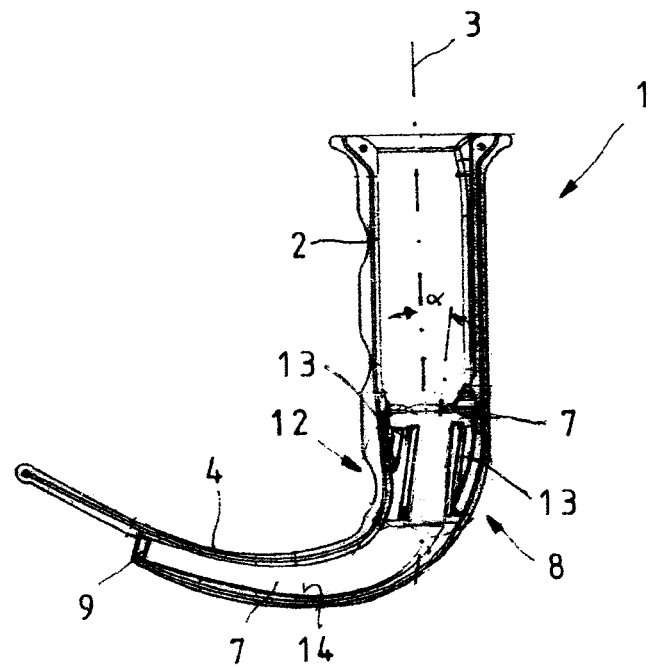
FIG. 3B shows a side view of another laryngoscope in cross section and rotated through 90°, the laryngoscope having ribs formed only in sections about the circumference of an inner channel wall of the laryngoscope.

The laryngoscope 1 shown in FIGS. 1 to 3 is composed of a handle 2 and of a blade 4 arranged at the distal end of the handle 2 at an angle with respect to the longitudinal axis 3 of the handle 2.

As will be seen from the figures, the blade 4 is oriented substantially at right angles to the longitudinal axis 3 of the handle 2. In practice, the angle at which the blade 4 is angled with respect to the longitudinal axis 3 of the handle 2 is 70° to 90°.

Laryngoscopes 1 of this kind, used as disposable articles, are generally made of a plastics material and are preferably formed from two shells produced by injection molding.

A channel 7 is formed in the laryngoscope 1 in order to permit insertion of an image carrier 5 of a video endoscope 6, which channel 7, in the transition area 8 from the handle 2 to the blade 4, merges in a radius from the handle 2 into the blade 4. For insertion of the image carrier 5, the channel 7 extending from the handle 2 into the blade 4 is open at the proximal end in the handle 2, while the distal end of the channel 7 located in the blade is generally closed by a window 9.

The component designated here as the image carrier 5 of the laryngoscope 1 is a cable 10 with a video chip 11 arranged at its distal end.

Since, on the one hand, the blade 4 is angled at an angle of 70° to 90° with respect to the longitudinal axis 3 of the handle 2 and thus the radius of the channel 7 in the transition area 8 from the handle 2 into the blade 4 is also very tight, and on the other hand, the image carrier 5 of the video endoscope 6 has a certain stiffness, there is a danger, upon insertion of the image carrier 5 into the channel 7, of the image carrier 5 hitting the ground in the radius of the transition area 8 and buckling. This buckling of the image carrier 5 can result in permanent damage to the image carrier 5 and, consequently, a deterioration of the image transmission.

To allow the image carrier 5 to be inserted through the channel 7 from the handle 2 into the blade 4 without buckling, at least one run-on bevel 12 is formed in the interior of the channel 7 of the laryngoscope 1 shown in FIGS. 1 and 2, specifically, as can be seen in particular from FIG. 2, in the transition area 8 from the handle 2 into the blade 4. The run-on bevel 12, narrowing the channel 7, serves as a guide for the image carrier 5 in the interior of the channel 7 and thus also makes it possible to guide the image carrier 5 round tight radii without buckling.

In the embodiment shown in FIG. 2, the run-on bevel 12 is composed of several ribs 13 arranged in parallel and at a distance from one another. This design reduces the weight, since less material needs to be used for the run-on bevel 12, and, by virtue of the ribs 13 extending parallel to one another, it additionally provides very good guiding of the image carrier 5 that is to be inserted into the channel 7.

To make it easier to insert the image carrier 5 in a targeted manner into the channel 7, the ribs 13 in the embodiment shown are oriented facing into the channel 7 at an angle α with respect to the longitudinal axis 3 of the handle 2. This angled orientation of the ribs 13 is such that the ribs 13 are arranged, facing into the radius, on the inner wall 14 of the channel 7.

Viewed in the direction of insertion of the image carrier 5 into the channel 7, the ribs 13 forming the run-on bevel 9 are provided on the inner wall 14 of the channel at a location proximal from the strongest curvature of the radius. This arrangement of the ribs 13 before the strongest curvature, in the direction of insertion, ensures that the image carrier 5 is guided at the correct angle, and without risk of buckling, into the transition area 8 between handle 2 and blade 4.

Figure 4:
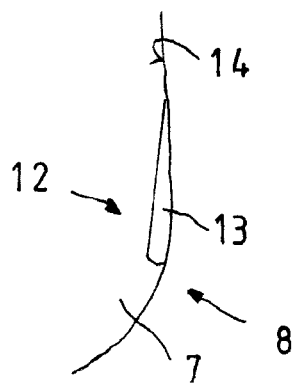
FIG. 4 shows a schematic side view of a rib.

As will be seen from FIG. 4, in addition to being at the angle α with respect to the longitudinal axis 3 of the handle 2, the ribs 13 can additionally be formed such that they also narrow the inside diameter of the channel 7, since they have an increasing radial thickness along their axial length from proximal to distal.

The arrangement of the ribs 13 on the inner wall 14 of the channel can be such that the ribs 13 are either formed all the way round the entire circumference of the inner wall 14 of the channel or are formed only in sections about the circumference of the inner wall 14 of the channel. In the case of the only sectional arrangement of the ribs 13, they can be divided up into one or more sections about the circumference of the inner wall 14 of the channel.

While being easy to handle, a laryngoscope 1 of the above-described design ensures that the image carrier 5 is inserted into the channel 7 in a manner that protects material.

The invention claimed is:

1. A laryngoscope, comprising:
   a handle;
   a blade at a distal end of the handle, the blade arranged at an angle to a longitudinal axis of the handle; and
   a channel for receiving an image carrier of a video endoscope, the channel formed in the handle and in the blade such that the channel, in a transition area from the handle to the blade, merges in a radius from the handle into the blade;
   wherein in the transition area from the handle into the blade, which is formed as the radius, at least one run-on bevel is formed in an interior of the channel and on an inner wall of the channel; and
   wherein the at least one run-on bevel is composed of several ribs arranged at a distance from one another.

2. The laryngoscope according to claim 1, wherein the ribs are arranged parallel to one another.

3. The laryngoscope according to claim 1, wherein the ribs, viewed in a direction of insertion of the image carrier, are arranged on the inner wall of the channel at a location proximal from a portion of the radius at which curvature of the radius is greatest.

4. The laryngoscope according to claim 1, wherein the ribs, facing into the channel, are oriented at an angle with respect to the longitudinal axis of the handle.

5. The laryngoscope according to claim 1, wherein the ribs have an increasing radial thickness along their axial length, from proximal to distal.

6. The laryngoscope according to claim 1, wherein the ribs are formed all the way round an entire circumference of the inner wall of the channel.

7. The laryngoscope according to claim 1, wherein the ribs are formed only in sections about a circumference of the inner wall of the channel.

8. The laryngoscope according to claim 1, wherein the angle at which the blade is angled with respect to the longitudinal axis of the handle is 70° to 90°.

9. The laryngoscope according to claim 1, wherein the handle and the blade are connected to each other releasably.

10. The laryngoscope according to claim 2, wherein the ribs, viewed in a direction of insertion of the image carrier, are arranged on an inner wall of the channel at a location proximal from a portion of the radius at which curvature of the radius is greatest.

11. A laryngoscope, comprising:
    a handle;
    a blade at a distal end of the handle, the blade arranged at an angle to a longitudinal axis of the handle; and
    a channel for receiving an image carrier of a video endoscope, the channel formed in the handle and in the blade such that the channel, in a transition area from the handle to the blade, merges in a radius from the handle into the blade;

wherein in the transition area from the handle into the blade, which is formed as the radius, at least one run-on bevel is formed in an interior of the channel;

wherein the at least one run-on bevel is composed of several ribs arranged at a distance from one another; and wherein the ribs have an increasing radial thickness along their axial length, from proximal to distal.

* * * * *